(12) United States Patent
Sung et al.

(10) Patent No.: US 9,228,190 B2
(45) Date of Patent: Jan. 5, 2016

(54) VECTOR FOR CONSTITUTIVE HIGH-LEVEL EXPRESSION CONTAINING REPE MUTANT GENE

(75) Inventors: Moon-Hee Sung, Daejeon (KR); Seung Pyo Hong, Daejeon (KR); A Ri Jang, Seoul (KR)

(73) Assignees: Bioleaders Corporation, Daejeon (KR); Kookmin University Industry-Academic Cooperation Foundation, Seoul (KR)

(*) Notice: Subject to any disclaimer, the term of this patent is extended or adjusted under 35 U.S.C. 154(b) by 743 days.

(21) Appl. No.: 13/143,918

(22) PCT Filed: Jan. 7, 2010

(86) PCT No.: PCT/KR2010/000109
§ 371 (c)(1),
(2), (4) Date: Sep. 6, 2011

(87) PCT Pub. No.: WO2010/079982
PCT Pub. Date: Jul. 15, 2010

(65) Prior Publication Data
US 2011/0312030 A1      Dec. 22, 2011

(30) Foreign Application Priority Data
Jan. 8, 2009   (KR) .................. 10-2009-0001509

(51) Int. Cl.
*C12N 15/00* (2006.01)
*C12P 21/06* (2006.01)
*C12N 1/20* (2006.01)
*C12N 15/70* (2006.01)
*C07K 14/195* (2006.01)
*C12N 15/74* (2006.01)

(52) U.S. Cl.
CPC .............. *C12N 15/70* (2013.01); *C07K 14/195* (2013.01); *C12N 15/746* (2013.01)

(58) Field of Classification Search
None
See application file for complete search history.

(56) References Cited

U.S. PATENT DOCUMENTS

2010/0196956 A1* 8/2010 Sung et al. ................... 435/69.1

FOREIGN PATENT DOCUMENTS

| KR | 10-0469800 B1 | 2/2005 |
| KR | 10-2008-0086161 A | 9/2008 |
| KR | 10-0872042 B1 | 12/2008 |

OTHER PUBLICATIONS

Sequence Alignment of AF104239 with Seq ID No: 2. Conducted on Sep. 9, 2013, wherein AF104239 is publicly available on Jan. 16, 1998; 3 pages.*
Karina A. Aires et al., "Production of Human Papillomavirus Type 16 L1 Virus-Like Particles by Recombinant *Lactobacillus casei* Cells", Applied and Environmental Microbiology, 2006, pp. 745-752, vol. 72, No. 1.
Teija Koivula et al., "Isolation and Characterization of *Lactococcus lactis* subsp. Lactis Promoters", Applied and Environmental Microbiology, 1991, pp. 333-340, vol. 57, No. 2.
Yasuo Kawasaki et al., "Mini-F Plasmid Mutants Able to Replicate in the Absence of $\sigma^{32}$: Mutations in the repE Coding Region Producing Hyperactive Initiator Protein", Journal of Bacteriology, 1991, 1064-1072, vol. 173, No. 3.
Satoko Maki et al., "DNA sequence of an amber replication mutant indicates that a 29 kd protein is the product of the F plasmid replication gene", Mol Gen Genet, 1984, pp. 337-339, vol. 194.
T. Maki et al., repE protein [*Lactococcus garvieae*], GenBank Accession No. YP_001798636, 2008.
Fujihiko Matsunaga et al., "DNA-Binding Domain of the RepE Initiator Protein of Mini-F Plasmid: Involvement of the Carboxyl-Terminal Region", Journal of Bacteriology, 1995, pp. 1994-2001, vol. 177, No. 8.
Tomio Morino et al., "Construction of a runaway vector and its use for a high-level expression of a cloned human superoxide dismutase gene", Applied Microbiology and Biotechnology, 1988, pp. 170-175, vol. 28.
A. Nakamura et al., "Structural basis for regulation of bifunctional roles in replication initiator protein", PNAS, 2007, pp. 18484-18489, vol. 104, No. 47.
A. Nakamura et al., "The N-terminal domain of the replication initiator protein RepE is a dimerization domain forming a stable dimer", Biochemical and Biophysical Research Communications, 2004, pp. 10-15, vol. 315.
Jos F.M.L. Seegers, *Lactobacilli* as live vaccine delivery vectors: progress and prospects, Trends in Biotechnology, 2002, pp. 508-515, vol. 20, No. 12.
H. Sletvold et al., Putative replication protein [*Enterococcus faecium*], GenBank Accession No. YP_002128409, 2008.
Philippe Slos et al., "Isolation and Characterization of Chromosomal Promoters of *Streptococcus salivarius* subsp. Thermophilus", Applied and Environmental Microbiology, 1991, pp. 1333-1339, vol. 57, No. 5.
Lothar Steidler et al., "Biological containment of genetically modified *Lactococcus lactis* for intestinal delivery of human interleukin 10", Nature Biotechnology, 2003, pp. 785-789, vol. 21, No. 7.
Takashi Tokino et al., "Purification and properties of the mini-F plasmid-encoded E protein needed for autonomous replication control of the plasmid", Proc. Natl. Acad. Sci. USA, 1986, pp. 4109-4113, vol. 83.
Ashhan Tolun et al., "Separation of the Minimal Replication Region of the F Plasmid into a Replication Origin Segment and a Trans-Acting Segment", Mol Gen Genet, 1982, pp. 372-377, vol. 186.

(Continued)

*Primary Examiner* — Catherine S Hibbert
*Assistant Examiner* — Channing S Mahatan
(74) *Attorney, Agent, or Firm* — Rabin & Berdo, P.C.

(57) ABSTRACT

A vector for constitutively expressing a high level of a target protein, and more particularly a RepE mutant protein containing a deletion of 21 amino acids in the C-terminal region of a RepE protein and a vector for constitutively expressing a high level of a target protein, which comprises a gene encoding the mutant protein. The constitutive high-level expression vector can stably express a high level of a target protein. Also, the surface expression vector can express a target protein on the surface of recombinant microorganisms while constitutively expressing a high level of the target protein, and thus will be useful for construction of an antigen for vaccines.

11 Claims, 3 Drawing Sheets

(56) References Cited

OTHER PUBLICATIONS

Jos M. B. M. Van Der Vossen et al., "Isolation and Characterization of *Streptococcus cremoris* Wg2-Specific Promoters", Applied and Environmental Microbiology, 1987, pp. 2452-2457, vol. 53, No. 10.
English Language Abstract of KR 10-2004-0032824 A which is the application publication of KR 10-0469800 B1.
English Language Abstract of KR 10-2007-0031248 A which is the application publication of KR 10-0872042 B1.
English Language Abstract of KR 10-2008-0086161 A.
International Search Report of PCT/KR2010/000109 mailed on Sep. 27, 2010.

* cited by examiner

*: TTA(Leu) → TGA (stop)

SEQUENCE LISTING

```
<160> NUMBER OF SEQ ID NOS: 10

<210> SEQ ID NO 1
<211> LENGTH: 474
<212> TYPE: PRT
<213> ORGANISM: Artificial
<220> FEATURE:
<223> OTHER INFORMATION: RepE variant

<400> SEQUENCE: 1

Met Asn Ile Pro Phe Val Val Glu Thr Val Leu His Asp Gly Leu Leu
1               5                   10                  15

Lys Tyr Lys Phe Lys Asn Ser Lys Ile Arg Ser Ile Thr Thr Lys Pro
            20                  25                  30

Gly Lys Ser Lys Gly Ala Ile Phe Ala Tyr Arg Ser Lys Ser Ser Met
        35                  40                  45

Ile Gly Gly Arg Gly Val Val Leu Thr Ser Glu Glu Ala Ile Gln Glu
    50                  55                  60

Asn Gln Asp Thr Phe Thr His Trp Thr Pro Asn Val Tyr Arg Tyr Gly
65                  70                  75                  80

Thr Tyr Ala Asp Glu Asn Arg Ser Tyr Thr Lys Gly His Ser Glu Asn
                85                  90                  95

Asn Leu Arg Gln Ile Asn Thr Phe Phe Ile Asp Phe Asp Ile His Thr
            100                 105                 110

Ala Lys Glu Thr Ile Ser Ala Ser Asp Ile Leu Thr Thr Ala Ile Asp
        115                 120                 125

Leu Gly Phe Met Pro Thr Met Ile Ile Lys Ser Asp Lys Gly Tyr Gln
    130                 135                 140

Ala Tyr Phe Val Leu Glu Thr Pro Val Tyr Val Thr Ser Lys Ser Glu
145                 150                 155                 160

Phe Lys Ser Val Lys Ala Ala Lys Ile Ile Ser Gln Asn Ile Arg Glu
                165                 170                 175

Tyr Phe Gly Lys Ser Leu Pro Val Asp Leu Thr Cys Asn His Phe Gly
            180                 185                 190
```

```
Ile Ala Arg Ile Pro Arg Thr Asp Asn Val Glu Phe Phe Asp Pro Asn
            195                 200                 205

Tyr Arg Tyr Ser Phe Lys Glu Trp Gln Asp Trp Ser Phe Lys Gln Thr
    210                 215                 220

Asp Asn Lys Gly Phe Thr Arg Ser Ser Leu Thr Val Leu Ser Gly Thr
225                 230                 235                 240

Glu Gly Lys Lys Gln Val Asp Glu Pro Trp Phe Asn Leu Leu Leu His
                245                 250                 255

Glu Thr Lys Phe Ser Gly Glu Lys Gly Leu Ile Gly Arg Asn Asn Val
                260                 265                 270

Met Phe Thr Leu Ser Leu Ala Tyr Phe Ser Ser Gly Tyr Ser Ile Glu
            275                 280                 285

Thr Cys Glu Tyr Asn Met Phe Glu Phe Asn Asn Arg Leu Asp Gln Pro
        290                 295                 300

Leu Glu Glu Lys Glu Val Ile Lys Ile Val Arg Ser Ala Tyr Ser Glu
305                 310                 315                 320

Asn Tyr Gln Gly Ala Asn Arg Glu Tyr Ile Thr Ile Leu Cys Lys Ala
                325                 330                 335

Trp Val Ser Ser Asp Leu Thr Ser Lys Asp Leu Phe Val Arg Gln Gly
                340                 345                 350

Trp Phe Lys Phe Lys Lys Arg Ser Glu Arg Gln Arg Val His Leu
            355                 360                 365

Ser Glu Trp Lys Glu Asp Leu Met Ala Tyr Ile Ser Glu Lys Ser Asp
            370                 375                 380

Val Tyr Lys Pro Tyr Leu Val Thr Thr Lys Lys Glu Ile Arg Glu Val
385                 390                 395                 400

Leu Gly Ile Pro Glu Arg Thr Leu Asp Lys Leu Leu Lys Val Leu Lys
                405                 410                 415

Ala Asn Gln Glu Ile Phe Phe Lys Ile Lys Pro Gly Arg Asn Gly Gly
                420                 425                 430

Ile Gln Leu Ala Ser Val Lys Ser Leu Leu Leu Ser Ile Ile Lys Val
            435                 440                 445

Lys Lys Glu Glu Lys Glu Ser Tyr Ile Lys Ala Leu Thr Asn Ser Phe
450                 455                 460

Asp Leu Glu His Thr Phe Ile Gln Glu Thr
465                 470
```

<210> SEQ ID NO 2
<211> LENGTH: 1425
<212> TYPE: DNA
<213> ORGANISM: Artificial
<220> FEATURE:
<223> OTHER INFORMATION: repE variant

<400> SEQUENCE: 2

```
atgaatatcc ttttgttgt agaaactgtg cttcatgacg gcttgttaaa gtacaaattt      60
aaaaatagta aaattcgctc aatcactacc aagccaggta aaagcaaagg ggctattttt     120
gcgtatcgct caaaatcaag catgattggc ggtcgtggtg ttgttctgac ttccgaggaa    180
gcgattcaag aaaatcaaga tacatttaca cattggacac ccaacgttta tcgttatgga    240
acgtatgcag acgaaaaccg ttcatacacg aaaggacatt ctgaaaacaa tttaagacaa    300
atcaatacct tctttattga ttttgatatt cacacggcaa agaaactat ttcagcaagc     360 gatattttaa caaccgctat tgatttaggt tttatgccta ctatgattat caaatctgat   420
aaaggttatc aagcatattt tgttttagaa acgccagtct atgtgacttc aaaatcagaa   480
```

-continued

```
tttaaatctg tcaaagcagc caaaataatt tcgcaaaata tccgagaata ttttggaaag      540
tctttgccag ttgatctaac gtgtaatcat tttggtattg ctcgcatacc aagaacggac      600
aatgtagaat tttttgatcc taattaccgt tattctttca agaatggca agattggtct       660 ttcaaacaaa cagataataa gggcttact cgttcaagtc taacggtttt aagcggtaca       720
gaaggcaaaa aacaagtaga tgaaccctgg tttaatctct tattgcacga aacgaaattt     780
tcaggagaaa agggtttaat agggcgtaat aacgtcatgt ttaccctctc tttagcctac     840
tttagttcag gctattcaat cgaaacgtgc gaatataata tgtttgagtt taataatcga    900
ttagatcaac ccttagaaga aaagaagta atcaaaattg ttagaagtgc ctattcagaa     960
aactatcaag gggctaatag ggaatacatt accattcttt gcaaagcttg ggtatcaagt   1020
gatttaacca gtaaagattt atttgtccgt caagggtggt ttaaattcaa gaaaaaaga    1080 agcgaacgtc aacgtgttca tttgtcagaa tggaagaag atttaatggc ttatattagc    1140
gaaaaaagcg atgtatacaa gccttattta gtgacgacca aaaagagat tagagaagtg    1200 ctaggcattc ctgaacggac attagataaa ttgctgaagg tactgaaggc gaatcaggaa   1260
attttcttta agattaaacc aggaagaaat ggtggcattc aacttgctag tgttaaatca    1320 tgttgctat cgatcattaa agtaaaaaaa gaagaaaag aaagctatat aaaggcgctg     1380
acaaattctt ttgacttaga gcatacattc attcaagaga cttga                    1425
```

<210> SEQ ID NO 3
<211> LENGTH: 26
<212> TYPE: DNA
<213> ORGANISM: Artificial
<220> FEATURE:
<223> OTHER INFORMATION: primer

<400> SEQUENCE: 3
cgcgcatgca atacccactt attgcg                                          26

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4
cagttctttt ttcatgtaga tatcctcc                                        28

<210> SEQ ID NO 5
<211> LENGTH: 28
<212> TYPE: DNA
<213> ORGANISM: Artificial
<220> FEATURE:
<223> OTHER INFORMATION: primer

<400> SEQUENCE: 5
ggaggatatc tacatgaaaa aagaactg                                        28

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6

```
ggcgctggcg gtcgtttgg                                              19

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
cggaaatcgt ttgattg                                                17

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
ctagcttgtt tcaagtctc                                              19

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
cattcaagag acttgaaaca ag                                          22

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
ctggtagttg tgtgaccgca atcgg                                       25
```

VECTOR FOR CONSTITUTIVE HIGH-LEVEL EXPRESSION CONTAINING REPE MUTANT GENE

TECHNICAL FIELD

The present invention relates to a vector for constitutively expressing a high level of a target protein, and more particularly to a RepE mutant protein containing a deletion of 21 amino acids in the C-terminal region of a RepE protein and to a vector for constitutively expressing a high level of a target protein, which comprises a gene encoding the mutant protein.

BACKGROUND ART

Recently, in USA and Europe, studies have been conducted on the development of live vaccines using lactic acid bacteria, and on vehicles for delivering useful hormone drugs into the intestines, and on the establishment of efficient genetic resources therefor and the development of insertion vectors for lactic acid bacteria. Particularly, the utility of lactic acid bacteria as vaccine vehicles has been highly evaluated, because unmethylated CpG DNA, lipoteichoic acid, peptidoglycan and the like, which are contained in lactic acid bacteria in large amounts, are known to function as adjuvants. In addition, lactic acid bacteria have many advantages in that they can induce intestinal mucosal immunity, because they show resistance to bile acid and gastric acid to make it possible to deliver antigens to the intestines (Jos F. M. K. Seegers, Trends Biotechnol., 20:508, 2002).

However, in order for lactic acid bacteria to be used as vaccine vehicles, it is required to develop a technology of presenting antigen proteins for the production of disease-preventing antibodies to the inside or outside of bacterial cells so as to allow antigen-antibody reactions to occur smoothly. In fact, various study results, which indicate that lactic acid bacteria are suitable as vaccine vehicles, have been reported. Examples of these studies include the examination of the antibody-inducing capacity of lactic acid bacteria, in which the L1 protein of human papilloma virus (HPV) is expressed in inside (Karina, A. A. et al., Appl. Environ. Microbiol., 72: 745, 2006), and the examination of the disease-treating effects of a lactic acid bacterial strain which secrets and expresses IL-2 (interleukin-2) (Lothar, S. et al., Nat. Biotechnol., 21:785, 2003). As described above, the development of various applications of lactic acid bacteria expressing target proteins, and scientific studies on the lactic acid bacteria, have been actively conducted, but there are problems in that the expression levels of the target proteins are insufficient and expression vectors are unstable in host cells.

Methods for producing foreign proteins in host cells include: a method of using a highly efficient promoter to increase the expression level of the protein; a cell surface display method of expressing a desired protein by attaching it onto the surface of host cells; and a method of increasing the copy number of an expression vector in host cells.

The cell surface display technology uses surface proteins of microorganisms, such as bacteria or yeasts, as a surface anchoring motif, to express a foreign protein on the surface and is used in various applications, including production of recombinant live vaccines, construction and screening of peptide/antibody library, whole cell absorbents, whole cell bioconversion catalysts, and the like. The application scope of this technology is determined according to the kind of protein to be expressed on the cell surface. Therefore, it is considered that the cell surface display technology can be used in a very broad range of applications.

Previously, the present inventors conducted studies on the use of a poly-gamma-glutamic acid synthetase complex gene (pgsBCA), derived from *Bacillus subtilis* sp., as a novel surface anchoring motif, and as a result, developed a novel vector for effectively expressing a foreign protein on the surface of microorganisms and a method for expressing large amounts of a foreign protein on the surface of microorganisms, using the pgsBCA gene (Korean Patent Registration No. 469800).

In a method of using a highly efficient promoter, Known promoters for producing foreign proteins in lactic acid bacteria include constitutive expression promoters derived from the genome of *Streptococcus thermophilus* A504, *Lactococcus lactis* MG1614 or *Lactococcus cremoris* Wg2 (Philippe, S. et al., *Appl. Envion. Microbial.*, 57:1333, 1991, Teija, K. et al., *Appl. Envion. Microbial.*, 57:333, 1991, J. M. van der Vossen et al., *Appl. Envion. Microbial.*, 53: 2452, 1987). Previously, the present inventors developed a constitutively high-expression vector containing an aldolase promoter derived from *Lactobacillus casei* (Korean Patent Laid-Open Publication No. 10-2008-0086161).

Also, studies on a method for increasing the copy number of an expression vector in a host cell have been conducted (Tomio, M. et al, *Appl. Microbiol. Biotechnol.* 28:170, 1988). In addition, studies on a method of changing the copy number of a plasmid in a cell using the RepE involved in the replication of the protein have also been conducted (Yashuo, K. et al., *J. Bacteriology*, 173:1064, 1991).

The RepE protein that is the replication initiator protein of the mini-F plasmid plays an important role in initiating replication from the origin, has a molecular weight of 29 kDa and binds to the 19-bp repeat sequence of ori2 (Maki, S. et al., *Mol. Gen. Genet.*, 194:337, 1984; Tolun, A. et al., *Mol. Gen. Genet.* 186:372, 1982). Also, it has been reported that the RepE protein is involved in regulation of the copy number of the plasmid, and the frequency of initiation of replication in ori2 is determined by the concentration of the RepE protein in cell, whereby determining the copy number of the plasmid is determined (Tokino, T. et al., *Proc. Natl. Acad. Sci.* USA 83:4109, 1986).

Thus, efforts have been made to the copy number and stability of the plasmid by regulating the RepE protein. Also, there have been studies that the copy number of the plasmid was increased by point mutation of RepE (Kawasaki, Y. et el., *J. Bacteriology,* 173:1064, 1991), as well as studies that a RepE mutant protein resulting from a frame shift of the C-terminal region of the RepE protein acts as a repressor of transcription of a target protein (Matsunaga, F. et al., *J. Bacteriology,* 177:1994, 1995).

Accordingly, the present inventors have made extensive efforts to an expression vector, which is stable in transformed recombinant microorganisms and expresses a highly level of a target protein in the recombinant microorganisms, and as a result, have found that an expression vector, which contains a gene encoding a RepE protein containing a deletion of 21 amino acids in the C-terminal region of the RepE protein, stably expresses a high level of a target protein, thereby completing the present invention.

DISCLOSURE OF INVENTION

It is an object of the present invention to provide a vector for constitutive high-level expression which is stably replicated in a transformed recombinant microorganism.

Another object of the present invention is to provide vector for constitutive high-level expression which can stably and constitutively express a target protein on the surface of a transformed recombinant microorganism.

Still another object of the present invention is to provide a recombinant microorganism transformed with said vector and a method of producing a target protein by culturing said recombinant microorganism.

To achieve the above objects, the present invention provides a RepE mutant protein having an amino acid sequence of SEQ ID NO: 1, which contains a deletion of 21 amino acids in the C-terminal region of the RepE protein.

The present invention also provides a repE mutant gene encoding the RepE mutant protein.

The present invention also provides a vector for constitutive high-level expression of a target protein, which comprises said repE mutant gene, and a target protein-encoding gene operably linked to the repE mutant gene.

The present invention also provides a recombinant microorganism transformed with said vector.

The present invention also provides a method for producing a target protein, the method comprising the steps of: culturing said recombinant microorganism to produce the target protein on the surface of the microorganism; and collecting the produced target protein.

The present invention also provides a surface expression vector for constitutively expressing a high level of a target protein, the surface expression vector comprising: said repE mutant gene; an aldolase promoter (Pald) derived from lactic acid bacteria; any one or more poly-gamma-glutamic acid synthetase complex genes selected from the group consisting of pgsB, pgsC and pgsA; and a gene encoding the target protein.

The present invention also provides a recombinant microorganism transformed with said vector.

The present invention also provides a method for producing a target protein, the method comprising the steps of: culturing said recombinant microorganism to produce the target protein on the surface of the microorganism; and collecting the produced target protein or collecting the microorganism having the target protein produced on the surface thereof.

BEST MODE FOR CARRYING OUT THE INVENTION

Figure 1:
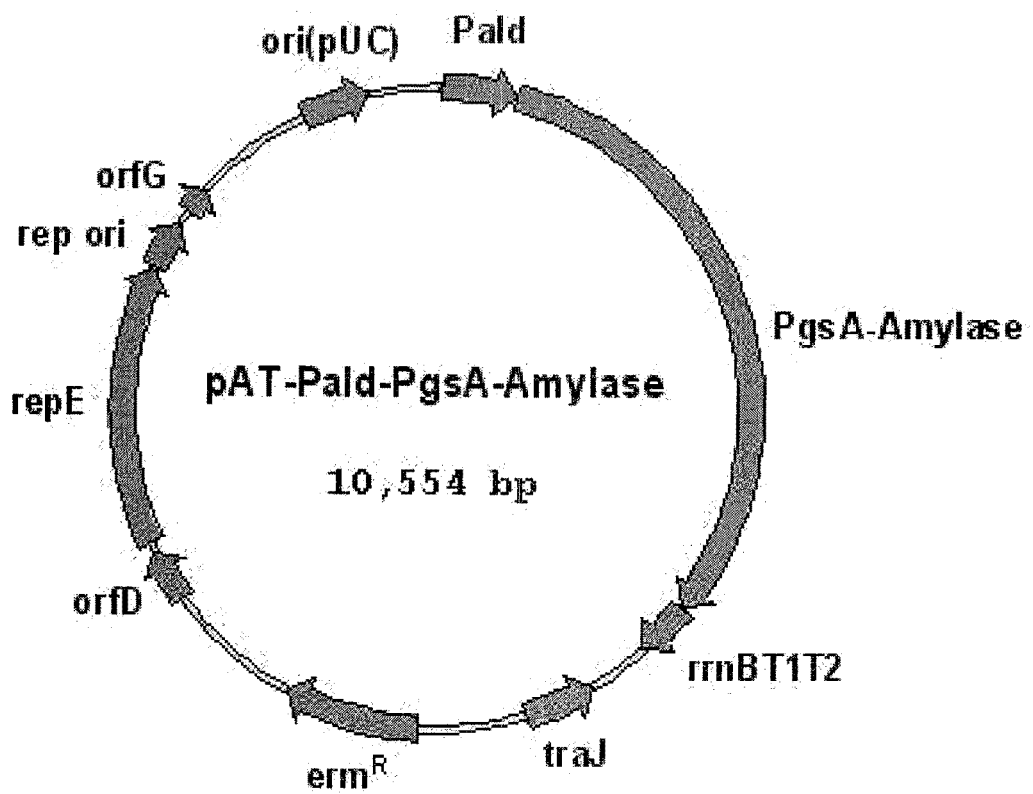
FIG. 1 is a genetic map of the constitutive high-level expression vector pAT-Pald-PgsA-Amylase which contains a non-mutated repE gene.
Figure 2:
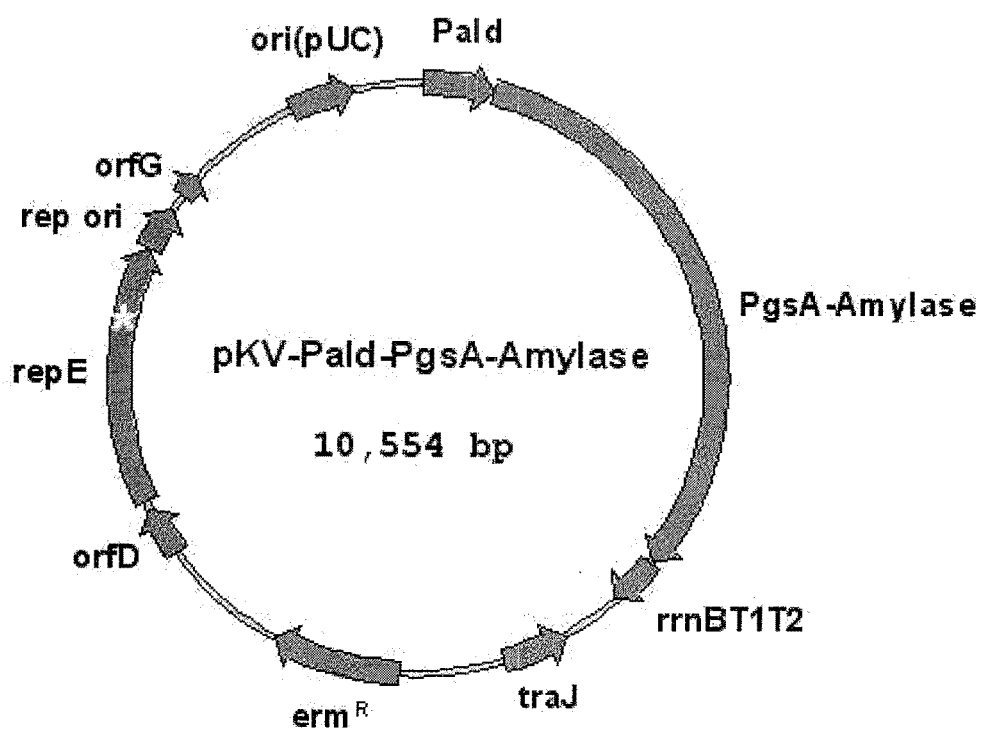
FIG. 2 is a genetic map of the constitutive high-level expression vector pKV-Pald-PgsA-Amylase which contains a gene encoding a RepE mutant protein containing a deletion of 21 amino acids in the C-terminal region of the RepE protein.

In one aspect, the present invention is directed to a RepE mutant protein having an amino acid sequence of SEQ ID NO: 1, which contains a deletion of 21 amino acids in the C-terminal region of the RepE protein, and a repE mutant gene encoding the RepE mutant protein.

The RepE protein binds to the origin of replication of the plasmid so that it is involved in the initiation of the replication. In the present invention, the RepE protein was mutated, thereby obtaining a RepE mutant protein in a recombinant microorganism transformed with an expression vector containing a gene encoding the RepE mutant protein, wherein the expression vector can stably express a high level of the RepE mutant protein.

In the present invention, each of the C-terminal, middle and N-terminal regions of the RepE protein in a plasmid containing the repE gene and an amylase gene as a target gene-encoding gene was mutated by site-directed-mutagenesis. The plasmid containing the mutated repE gene was transformed into lactic acid bacteria, and the activity of an amylase produced by the transformed bacteria was examined. As a result, it was found that only the vector which contains the gene encoding the RepE mutant protein containing a deletion of 21 amino acids in the C-terminal region of the RepE protein constantly maintains high amylase activity in the transformed lactic acid bacteria. On the basis of this finding, the RepE mutant protein containing a deletion of 21 amino acids in the C-terminal region was selected as a RepE mutant protein for a constitutive high-expression vector.

Preferably, the repE mutant gene encoding the RepE mutant protein may have a base sequence of SEQ ID NO: 2.

In another aspect, the present invention is directed to a vector for constitutive high-level expression of a target protein, which comprises said repE mutant gene, and a target protein-encoding gene operably linked to the repE mutant gene, and a recombinant microorganism transformed with said vector.

Generally, an expression vector minimally requires a promoter enabling transcription, a gene expressing a target protein downstream of the promoter, a gene which can be amplified by self-replication in microorganisms, and an antibiotic selection marker gene for selecting a target vector, in which the genes except for the target gene can vary depending on the backbone of the vector and a selected host cell. The genes minimally required in vector construction are widely known to those skilled in the art and can be easily selected depending on the expression conditions and intended use of a target gene.

Various methods and means may be used to introduce a vector or DNA sequence for expressing not only a target protein, but also a gene containing a regulatory region, into an appropriate host cell. For example, biochemical methods, such as transformation, transfection, conjugation, protoplast fusion and calcium phosphate precipitation, or physical methods, such as DEAE (diethylaminoethyl) dextran and electroporation, may be used.

After the expression vector has been introduced into an appropriate host cell, only transformants can be screened using conventional techniques known in the art. In other words, transformants containing the vector capable of expressing a target gene can be screened using a selection medium suitable for the growth of host cells containing antibiotic substances.

As used herein, the term "target protein" or "foreign protein" means a protein which is not normally present in the transformed host cells expressing the protein. For example, when a virus-derived or tumor-derived protein is manipulated to be artificially expressed in lactic acid bacteria, the protein will be referred to as "foreign protein" or "target protein".

In the present invention, nucleic acid is "operably linked" when it is placed into a functional relationship with another nucleic acid sequence. This may mean the way in which gene and control sequence(s) are linked, in that the expression of the gene is possible when a suitable molecule (for example, transcription-activating protein) is combined with control sequence(s). For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

In still another aspect, the present invention is directed to a method for producing a target protein, the method comprising the steps of: culturing said recombinant microorganism to produce the target protein; and collecting the produced target protein.

The culture of the recombinant microorganism according to the present invention can be carried out according to a widely known method, and conditions including the culture temperature and time, the pH of medium, and the like can be suitably controlled. Collection of the recombinant microbial cells can be carried out using conventional isolation techniques, for example, centrifugation or molecular weight cut-off.

In yet another aspect, the present invention is directed to a surface expression vector for constitutively expressing a high level of a target protein, the surface expression vector comprising: said repE mutant gene; an aldolase promoter (Pald) derived from lactic acid bacteria; any one or more poly-gamma-glutamic acid synthetase complex genes selected from the group consisting of pgsB, pgsC and pgsA; and a gene encoding the target protein and a recombinant microorganism transformed with said vector.

In the present invention, an aldolase promoter that is a constitutive high-level expression promoter was used. The promoter serves to induce the expression of the aldolase gene in *Lactobacillus casei*.

The downstream of the promoter contains a poly-gamma glutamic acid synthetase complex gene, which is a surface anchoring motif, located between the promoter and the target protein in the DNA sequence of the vector. The gene of the surface anchoring motif plays a decisive role in the surface expression of the target gene, because it is linked to the initial portion of the target protein so as to induce the expressed protein to bind to lipid of the cell membrane, after it has been encoded into amino acids. A method of linking the gene of the surface anchoring motif with the promoter and the target gene can be performed by conventional techniques which can be easily practiced by those skilled in the art, including PCR, restriction enzyme digestion and ligation.

The surface anchoring motif used in the present invention was pgsA that is a poly-gamma-glutamic acid synthetase complex gene (pgsBCA).

A target protein, which is expressed by the promoter of the present invention and presented on the surface of the host cell, may be an enzyme, an antibody, an antigen, an adsorbing protein or an adhesion protein. Preferably, the target protein may be an antigen.

The target proteins or antigens include, but are not limited to, infectious microorganisms, immune disease-derived antigens or tumor-derived antigens, for example, fungal pathogens, bacteria, parasites, helminths, viruses or allergy-causing substances. More specifically, the antigens include tetanus toxoid, hemagglutinin molecule or nuclear protein of influenza virus, diphtheria toxoid, HIV gp120 or its fragments, HIV gag protein, IgA protease, insulin peptide B, *Spongospora subterranea* antigens, *Vibriose* antigens, *Salmonella* antigens, *Pneumococcus* antigens, respiratory syncytial virus antigens, *Haemophilus influenza* outer membrane protein, *Streptococcus pneumoniae* antigen, *Helicobacter pylori* urease, *Neisseria meningitidis* pilins, *N. gonorrhoeae* pilins, melanoma-associated antigens (TRP-2, MAGE-1, MAGE-3, gp-100, tyrosinase, MART-1, HSP-70, beta-HCG), human papilloma virus antigens E1, E2, E6 and E7 derived from HPV type 16, 18, 31, 33, 35 or 45, tumor antigen CEA, normal or mutant ras protein, normal or mutant p53 protein, Muc1, pSA, as well as antigens well known in the art, which are derived from the following: cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, Addison's disease, immunogens, allergen, cancer including solid and blood borne tumors, acquired immune deficiency syndrome, and factors involved in transplant rejection, such as kidney, heart, pancreas, lung, bone, and liver transplant rejections, and antigens inducing autoimmunity.

As used herein, the term "hosts" or "microorganisms" refers to lactic acid bacteria that are probiotic gram-positive bacteria, and common criteria used for selecting probiotic microorganisms include the following: (i) a microorganism derived from humans; (ii) stability against bile, acid, enzyme and oxygen; (iii) ability to adhere to intestinal mucosa; (iv) colonization potential in the human gastrointestinal tract; (v) production of antimicrobial substances; and (vi) demonstrable efficacy and safety. On the basis of such criteria, it is apparent that lactic acid bacteria are biocompatible and harmless to the human body. Thus, when transformants which use lactic acid bacteria as hosts are applied to the human body in order to deliver a gene or protein for preventing or treating disease, a step of detoxifying bacterial strains is not required, unlike a conventional method for preparing vaccines which uses bacterial strains.

In the present invention, the transformed microorganisms may be lactic acid bacteria or *E. coli*.

In the present invention, the lactic acid bacteria that are used as the host may include *Lactobacillus* sp., *Streptococcus* sp., and *Bifidobacterium* sp. Typically, *Lactobacillus* sp. includes *L. acidophilus*, *L. casei*, *L. plantarum*, *L. ferementum*, *L. delbrueckii*, *L. johnsonii* LJI, *L. reuteri* and *L. bulgaricus*; *Streptococcus* sp. includes *S. thermophilus*; and *Bifidobacterium* sp. includes *B. infantis*, *B. bifidum*, *B. longum*, *B. psuedolongum*, *B. breve*, *B. lactis* Bb-12, and *B. adolescentis*. Preferred is *Lactobacillus* sp.

In the present invention, an expression vector (pKV-PgsAL-Amylase), which contains a base sequence linked with the RepE mutant gene, the promoter and the surface anchoring motif pgsA and can express an alpha-amylase gene as a target gene, was constructed. The expression vector was inserted into *L. casei*, thus preparing transformants expressing amylase.

The target protein, which is expressed by the inventive promoter having an enhanced ability to express a gene, is expressed on the surface of microorganisms, and thus the transformed microorganisms of the present invention can be used as vaccines.

In a further aspect, the present invention is directed to a method for producing a target protein, the method comprising the steps of: culturing said recombinant microorganism to produce the target protein on the surface of the microorganism; and collecting the produced target protein or collecting the microorganism having the target protein produced on the surface thereof.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

Construction of Amylase Surface Expression Vector (pAT-Pald-PgsA-Amylase) Using Aldolase Promoter and Observation of Amylase Activity by Transformation of Lactic Acid Bacteria In order to construct a constitutive high-level expression vector, the promoter and replication-related portion of a vector capable of expressing a target protein on the surface of gram-negative or gram-positive microorganisms using pgsA (a poly-gamma-glutamic acid synthase complex gene derived from *Bacillus* sp. strains) were improved such that the vector can more stably express a high level of the target protein in a lactic acid bacteria host. As a result, the RepE protein that is involved in the initiation of replication of the plasmid was mutated and used for construction of a vector, thereby obtaining the constitutive high-level expression vector pKV-Pald-PgsAL-Amylase which is more stably replicated and maintained in host cells.

In this Example, a lactic acid bacteria-*E. coli* shuttle vector containing an aldolase promoter for increasing the expression level of a target protein in lactic acid bacteria was constructed.

First, in order to increase the expression level of a target protein in lactic acid bacteria, a fragment of an aldolase promoter derived from *Lactobacillus casei* was obtained. An aldolase promoter fragment was prepared by PCR using pDT-PgsA-Amylase (as described in Korean Patent Laid-Open Publication No. 10-2008-0086161) as a template with primers of SEQ ID NO: 3 and SEQ ID NO: 4.

```
SEQ ID NO: 3:
5"-CGC GCA TGC AAT ACC CAC TTA TTG CG-3

SEQ ID NO: 4:
5'-cag ttc ttt ttt cat gta gat atc ctc c-3'
```

As a result, a 421-bp DNA fragment containing the aldolase promoter, a SphI restriction enzyme site at the 5' terminal end and a 17-bp N-terminal fragment of pgsA at the 3' terminal end was obtained. A pgsA gene portion which can be linked with the above-prepared aldolase promoter fragment was prepared by PCR using the pDT-PgsA-Amylase vector as a template with primers of SEQ ID NOS: 5 and SEQ ID NO: 6.

```
SEQ ID NO: 5:
5'-gga gga tat cta cat gaa aaa aga act g-3'

SEQ ID NO: 6:
5'-ggc gct ggc ggt cgt ttg g-3'
```

As a result, a 782-bp DNA fragment containing a 13-bp 3'-terminal fragment of the aldolase promoter at the N-terminal end and pgsA linked thereto was obtained. The pgsA portion of the fragment contained a PstI restriction enzyme site.

The above-prepared two fragments were linked with each other and amplified by PCR using primers corresponding to both ends, thereby obtaining a 1175-bp DNA fragment. The DNA fragment was digested with SphI and PstI to obtaining a fragment containing the aldolase promoter and a portion and a portion of the N-terminal region of pgsA.

pBT:pgsA-Amylase (pAT-PslpA-pgsA-amylase; see Indirect Examples of Korean Patent Registration No. 0872042) was digested with the restriction enzymes SphI and PstI to remove the SlpA7 portion and the N-terminal portion of pgsA. The resulting product was used as the backbone of the expression vector.

The aldolase promoter-containing DNA fragment digested with the restriction enzymes SphI and PstI was linked with the pBT:pgsA-Amylase digested with the same restriction enzymes, thereby preparing pAT-Pald-PgsA-Amylase (FIG. 1).

The obtained pAT-Pald-PgsA-Amylase was repeatedly transformed into *Lactobacillus casei* by electroporation, but a transformant showing activity in 1% starch-containing solid MRS medium could not be obtained.

Example 2

Preparation of repE Mutant Gene (pKV)-Containing Amylase Expressing *E. coli*-Lactic Acid Bacteria Shuttle Vector (pKV-Pald-PgsAL-Amylase) and Observation of Amylase Activity in Lactic Acid Bacteria Transformants A gene encoding the RepE protein known to be involved in the initiation of replication of the plasmid in cells was mutated, thereby preparing an *E. coli*-lactic acid bacteria shuttle vector for inducing the expression of a target protein on the surface of lactic acid bacteria.

Each of the N-terminal, middle and C-terminal regions of the repE gene was mutated by site-directed mutagenesis, and the plasmid containing the mutated repE gene was transformed into *L. casei*. The amylase activities of the obtained transformants were compared with each other.

In order to mutate the C-terminal region of the repE gene contained in pAT-Pald-PgsA-Amylase, PCR was performed in the following manner. The resulting DNA fragments were linked with each other and subjected to site-directed mutagenesis so as to change the base sequence of a specific region thereof. First, a DNA fragment was obtained by PCR using pAT-Pald-PgsA-Amylase as a template with each of a primer pair of SEQ ID NO: 7 and SEQ ID NO: 8 and a primer pair of SEQ ID NO: 9 and SEQ ID NO: 10.

```
SEQ ID NO: 7:
5'-cgg aaa tcg ttt gat tg-3'

SEQ ID NO: 8:
5'-cta gct tgt ttc aag tct c-3'

SEQ ID NO: 9:
5'-cat tca aga gac ttg aaa caa g-3'

SEQ ID NO: 10:
5'-ctg gta gtt gtg tga ccg caa tcg g-3'
```

The obtained two fragments were linked with each other and amplified by PCR using primers corresponding to both ends, thereby obtaining a 3,888-bp DNA fragment. The obtained fragment had a T-to-G mutation at position 1,424 of the repE gene. The mutated fragment was digested with HindIII and PvuII, thereby obtaining 2,192-bp DNA fragment containing the C-terminal region of the repE gene and a replication-related portion.

The pAT-Pald-PgsA-Amylase was digested with each of a pair of PvuII and BamHI and a pair of BamHI and HindIII, thereby obtaining a 1,770-bp DNA fragment containing the pgsA gene, and a 6,582-bp DNA fragment containing an erythromycin antibiotic-resistant gene.

The C-terminal fragment of the repE gene mutated by site-directed mutagenesis was linked with the 1,770-bp DNA fragment and the 6,582-bp DNA fragment, thereby obtaining the *E. coli*-lactic acid bacterial shuttle vector pKV-Pald-PgsA-Amylase (mutant pAT-Pald-PgsA-Amylase) containing the repE mutant gene.

The pAT-Pald-PgsA-Amylase vector containing the repE mutant gene was transformed into *E. coli*, and the cells transformed with the vector having the correct mutation were collected. The plasmid was separated from the collected transformants, and the obtained plasmid vector was transformed into *L. casei*. Then, the transformed *L. casei* cells were cultured in 1% starch-containing MRS solid medium, after which the degree of degradation of starch by the amylase expressed on the surface of the *L. casei* cells examined by iodine staining.

Figure 3:
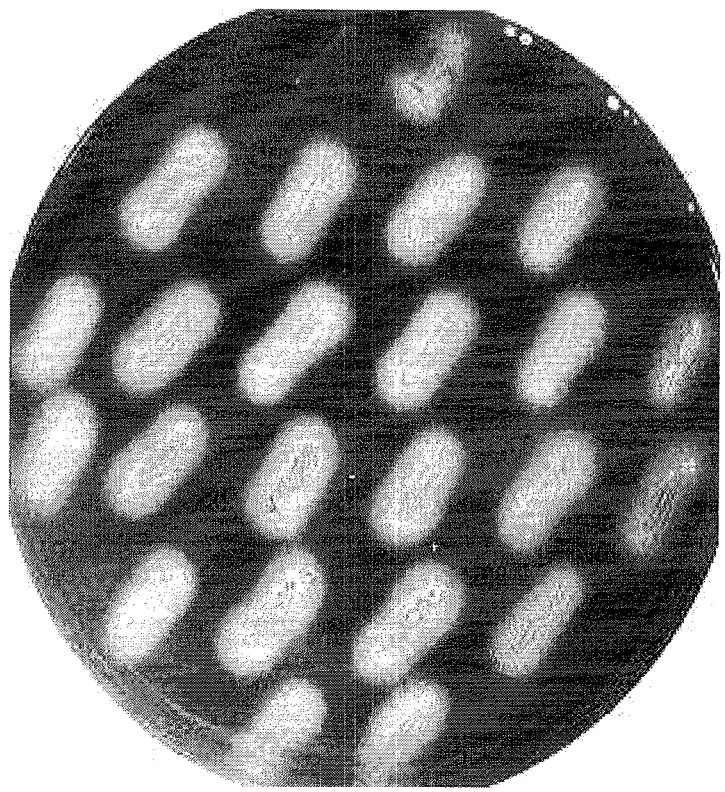
FIG. 3 shows the results of color reaction of iodine carried out to examine the starch-degrading ability of an amylase produced by a *Lactobacillus casei* strain transformed with the vector pKV-Pald-PgsA-Amylase.

As a result, it was observed that the plasmid vector having a gene encoding the RepE mutant protein (having a Leu (TTA)-to-stop codon (TGA) mutation at position 475 of the RepE protein and containing a deletion of 21 amino acids in the C-terminal region of the RepE protein) stably and strongly expressed the amylase gene in all the 50 transformants (FIG. 3).

INDUSTRIAL APPLICABILITY

The constitutive high-level expression vector according to the present invention can stably express a high level of a target protein. Also, the surface expression vector according to the present invention can express a target protein on the surface of recombinant microorganisms while constitutively expressing a high level of the target protein, and thus will be useful for construction of an antigen for vaccines.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claim is:

1. A vector for constitutive high-level expression of a target protein, which comprises a RepE mutant gene encoding a RepE mutant protein having an amino acid sequence of SEQ ID NO:1, which contains a deletion of 21 amino acids in the C-terminal region of the RepE protein, and a target protein-encoding gene operably linked to the RepE mutant gene.

2. The vector according to claim 1, wherein the RepE mutant gene has a base sequence of SEQ ID NO: 2.

3. A recombinant microorganism transformed with the vector of claim 2.

4. A method for producing a target protein, the method comprising the steps of: culturing the recombinant microorganism of claim 3 to produce the target protein; and collecting the produced target protein.

5. A surface expression vector for constitutively expressing a high level of a target protein, the surface expression vector comprising: a RepE mutant gene encoding a RepE mutant protein having an amino acid sequence of SEQ ID NO:1, which contains a deletion of 21 amino acids in the C-terminal region of the RepE protein; an aldolase promoter (Paid) from lactic acid bacteria; any one or more poly-gamma-glutamic acid synthetase complex genes selected from the group consisting of pgsB, pgsC and pgsA; and a gene encoding the target protein.

6. The surface expression vector according to claim 5, wherein the RepE mutant gene has a base sequence of SEQ ID NO: 2.

7. The surface expression vector according to claim 5, which is an *E. coli*-lactic acid bacteria shuttle vector.

8. The surface expression vector according to claim 5, wherein the target protein is an antigen.

9. A recombinant microorganism transformed with the vector of claim 5.

10. The recombinant microorganism according to claim 9, which is lactic acid bacteria or *E. coli*.

11. A method for producing a target protein, the method comprising the steps of: culturing the recombinant microorganism of claim 9 to produce the target protein on the surface of the microorganism; and collecting the produced target protein or collecting the microorganism having the target protein produced on the surface thereof.

\* \* \* \* \*